United States Patent
Liu et al.

(10) Patent No.: US 12,178,928 B2
(45) Date of Patent: Dec. 31, 2024

(54) ORAL IRRIGATOR

(71) Applicant: FLY CAT ELECTRICAL CO., LTD., Guangdong (CN)

(72) Inventors: Xinquan Liu, Guangdong (CN); Yong Tang, Guangdong (CN)

(73) Assignee: FLY CAT ELECTRICAL CO., LTD., Guangdong (CN)

( * ) Notice: Subject to any disclaimer, the term of this patent is extended or adjusted under 35 U.S.C. 154(b) by 194 days.

(21) Appl. No.: 17/723,854

(22) Filed: Apr. 19, 2022

(65) Prior Publication Data
US 2022/0331466 A1  Oct. 20, 2022

(30) Foreign Application Priority Data
Apr. 20, 2021  (CN) .......................... 202120819993.0

(51) Int. Cl.
*A61L 2/10* (2006.01)
*A61C 17/02* (2006.01)
*A61L 2/26* (2006.01)

(52) U.S. Cl.
CPC ............ *A61L 2/10* (2013.01); *A61C 17/0202* (2013.01); *A61L 2/26* (2013.01); *A61L 2202/11* (2013.01); *A61L 2202/24* (2013.01)

(58) Field of Classification Search
CPC .......... A61L 2/10; A61L 2202/11; A61L 2/26; A61L 2202/122; A61L 2/0029; A61L 2/0047; A61C 1/0076; A61C 17/02; A61C 19/002; A61C 17/0202
USPC ................................................ 433/82, 80, 89
See application file for complete search history.

(56) References Cited

U.S. PATENT DOCUMENTS

| | | | | |
|---|---|---|---|---|
| 5,935,431 A | * | 8/1999 | Korin | C02F 1/28 433/80 |
| 7,081,225 B1 | * | 7/2006 | Hollander | C02F 1/325 313/635 |
| 11,684,685 B1 | * | 6/2023 | Gonzalez | A61L 2/10 250/455.11 |

(Continued)

FOREIGN PATENT DOCUMENTS

| | | | | | |
|---|---|---|---|---|---|
| CN | 111671538 A | * | 9/2020 | | A61C 17/02 |
| CN | 112386353 A | * | 2/2021 | | A61C 17/02 |

(Continued)

OTHER PUBLICATIONS

CN 111671538 machine translation (Year: 2020).*
CN 215778815 machine translation (Year: 2022).*
KR 20090011235 machine translation (Year: 2009).*

*Primary Examiner* — Ralph A Lewis
(74) *Attorney, Agent, or Firm* — CANTOR COLBURN LLP

(57) ABSTRACT

The present application relates to an oral irrigator, the oral irrigator includes at least a main body, a partition wall, a sterilization portion, and a control main board. By providing the partition wall, the first cavity and the second cavity are separated from each other, and the spray head is separately accommodated in the second cavity, and the first cavity is provided with the sterilization portion corresponding to the second cavity. The sterilization portion includes a UV lamp module. The second cavity and the spray head are sterilized through the UV lamp module, which effectively reduces the secondary pollution of the flushing fluid.

10 Claims, 3 Drawing Sheets

(56) References Cited

U.S. PATENT DOCUMENTS

| | | | | |
|---|---|---|---|---|
| 2003/0190254 A1* | 10/2003 | Falat | .................... | A61C 1/0076 |
| | | | | 422/4 |
| 2010/0239998 A1* | 9/2010 | Snyder | .................. | A61C 19/06 |
| | | | | 433/29 |
| 2012/0141952 A1* | 6/2012 | Snyder | ............... | A61C 17/0202 |
| | | | | 433/82 |
| 2017/0100494 A1* | 4/2017 | Dobrinsky | ............. | A23C 3/076 |
| 2021/0308298 A1* | 10/2021 | Hsieh | ........................ | A61L 2/20 |
| 2022/0096673 A1* | 3/2022 | Yang | ........................ | A61L 2/10 |

FOREIGN PATENT DOCUMENTS

| | | | | | |
|---|---|---|---|---|---|
| CN | 215778815 U | * | 2/2022 | | |
| CN | 114376436 A | * | 4/2022 | | |
| CN | 114569747 A | * | 6/2022 | | |
| KR | 20090011235 U | * | 11/2009 | | |
| WO | WO-0128006 A2 | * | 4/2001 | ......... | G06K 7/10881 |
| WO | WO-2017048877 A1 | * | 3/2017 | ............... | A61L 2/10 |
| WO | WO-2021085949 A1 | * | 5/2021 | ........... | A61C 1/0076 |

\* cited by examiner

ORAL IRRIGATOR

CROSS REFERENCE TO RELATED APPLICATION

The present application claims priority to Chinese patent application No. 202120819993.0, filed on Apr. 20, 2021, the entire content of which is incorporated herein by reference.

TECHNICAL FIELD

The present application relates to the technical field of oral cleaning, and more particularly to an oral irrigator.

BACKGROUND

In the related art, the inside of the main body and the nozzle of the dental flusher are likely to breed bacteria because being in a humid environment all the year round, and it is easy to cause secondary pollution to the injected oral irrigating fluid, which in turn causes discomfort for the user when cleaning the dental cavity, causing poor experience of the user.

SUMMARY

Based on above-mentioned, it is necessary to provide an oral irrigator, so as to reduce the problem of secondary contamination of the flushing fluid sprayed by the oral irrigator in the related art.

In order to achieve the object above-mentioned, the present application provides an oral irrigator, which includes:
 a main body, provided therein with a cavity;
 a partition wall, arranged in the cavity along a longitudinal direction of the main body to divide the cavity into a first cavity and a second cavity spaced apart from each other, wherein the first cavity is configured for accommodating a working part, and the second cavity is configured for accommodating a spray head;
 a sterilization portion, located in the first cavity and arranged adjacent to the partition wall, wherein the sterilization portion comprises an ultraviolet light UV lamp module, the partition wall is provided with a light-transmitting area, such that light emitted by the UV lamp module passing through the light-transmitting area to irradiate an inside of the second cavity and the spray head; and
 a control main board, electrically connected to the UV lamp module, wherein the control main board is provided with a control switch group electrically connected to the control main board, and the control switch group comprises a UV control switch configured for controlling on and off of the UV lamp module.

In one of embodiments, the control switch group further includes an anti-inversion switch electrically connected to the control main board, and the anti-inversion switch is configured to respond to turn off the UV lamp module when the oral irrigator is in a tilted or inverted posture.

In one of embodiments, the control switch group further includes a timing switch electrically connected to the control main board, and the timing switch is configured to turn off the UV lamp module when a preset time period is reached.

In one of embodiments, a support member is provided in the first cavity; and the sterilization portion and the control main board are fixed in the first cavity through the support member.

In one of embodiments, the support member is arranged outside the working part to space the working part with the sterilization portion and the control main board.

In one of embodiments, an engagement portion is provided in the second cavity, and the spray head is suspended in the second cavity by means of the engagement portion.

In one of embodiments, a position of the light-transmitting area corresponds to an output end of the spray head.

In one of embodiments, the UV lamp module includes a substrate and UV lamp beads, and the UV lamp beads are provided on a side of the substrate facing the light-transmitting area.

In one of embodiments, the light-transmitting area is provided with an opening, and a light-transmitting plate is provided in the opening; and light-transmitting plate is a quartz glass plate.

In one of embodiments, the device further includes a battery arranged in the first cavity, and the battery is electrically connected to the control main board.

The above-mentioned oral irrigator includes at least a main body, a partition wall, a sterilization portion, and a control main board. By providing the partition wall, the first cavity and the second cavity are separated from each other, and the spray head is separately accommodated in the second cavity, and the first cavity is provided with the sterilization portion corresponding to the second cavity. The sterilization portion includes a UV lamp module. The second cavity and the spray head are sterilized through the UV lamp module, which effectively reduces the secondary pollution of the flushing fluid. Since the sterilization portion is built into the main body, while it can be disinfected and sterilized, the ultraviolet light emitted by the UV lamp module will not directly hit the eyes and human skin, and it is not easy to be touched by people, which has a certain degree of safety.

The additional aspects and advantages of the embodiments of the present application will be partly given in the following description, and part of them will become obvious from the following description, or be understood through the practice of the embodiments of the present application.

BRIEF DESCRIPTION OF THE DRAWINGS

The drawings constituting a part of the present application are used to provide a further understanding of the present application. The exemplary embodiments and descriptions of the present application are used to explain the present application, and do not constitute an improper limitation of the present application.

In order to more clearly describe the technical solutions in the embodiments of the present application, the following will briefly introduce the drawings needed in the description of the embodiments. Obviously, the drawings in the following description are only some embodiments of the present application. For those skilled in the art, without creative work, other drawings can be obtained based on these drawings.

Figure 1:
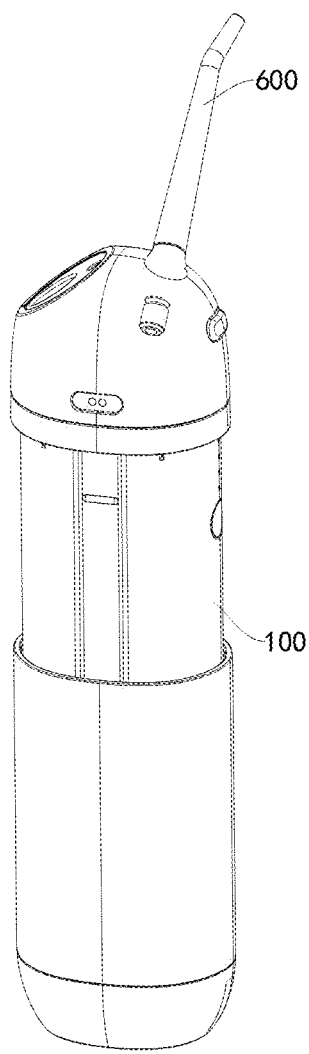
FIG. 1 is a schematic structural view of an oral irrigator in one implementation provided by an embodiment of the present application.

In the drawings, the technical features are listed:
 100—main body; 110—first cavity; 120—second cavity; 130—support member; 140—engagement portion; 200—partition wall; 210—light-transmitting area 300—UV lamp module;
400—control main board;
500—working part;
600—spray head;
700—battery;
800—switch button.

DETAILED DESCRIPTION OF THE EMBODIMENTS

In order to make the above objectives, features and advantages of the present application more obvious and easy to understand, the specific implementation of the present application will be described in detail below with reference to the accompanying drawings. In the following description, many specific details are explained in order to fully understand the present application. However, the present application can be implemented in many other ways different from those described here, and those skilled in the art can make similar improvements without departing from the connotation of the present application. Therefore, the present application is not limited to the specific embodiments disclosed below.

In the description of the present limit, it should be understood that the terms "center", "longitudinal", "transverse", "length", "width", "thickness", "upper", "lower", "front", "back", "left", "right", "vertical", "horizontal", "top", "bottom", "inner", "outer", "clockwise", "counterclockwise", "axial" "radial", "circumferential", etc. indicate the orientation or positional relationship based on the orientation or positional relationship shown in the drawings, only for the convenience of describing the present application and simplifying the present application, rather than indicating or implying. The device or element must have a specific orientation, be constructed and operated in a specific orientation, and therefore cannot be understood as a limitation of the present application.

In addition, the terms "first", "second", and "third" are only used for descriptive purposes, and cannot be understood as indicating or implying relative importance or implicitly indicating the number of indicated technical features. Thus, the features defined with "first", "second", and "third" may explicitly or implicitly include at least one of the features. In the description of the present application, a plurality of means at least two, such as two, three, etc., unless otherwise specifically defined.

In the present application, unless otherwise clearly specified and limited, the terms "installed", "connected", "connecting", "fixed" and other terms should be understood in a broad sense, for example, it can be a fixed connection or a detachable connection, or integrated; it can be mechanically connected or electrically connected; it can be directly connected or indirectly connected through an intermediary, and it can be the internal communication of two components or the interaction relationship between two components, unless otherwise clearly defined. For those skilled in the art, the specific meaning of the above-mentioned terms in the present application can be understood according to specific conditions.

In the present application, unless otherwise clearly defined and defined, the first feature "on" or "under" the second feature may be in direct contact with the first and second features or the first and second features may indirect contact through an intermediary. Moreover, the "above" of the first feature on the second feature may mean that the first feature is directly above or obliquely above the second feature, or it simply means that the level of the first feature is higher than that of the second feature. The "below" of the second feature of the first feature may mean that the first feature is directly below or obliquely below the second feature, or it simply means that the level of the first feature is smaller than the second feature.

It should be noted that when an element is referred to as being "fixed to" or "disposed on" another element, it can be directly on the other element or a central element may also be present. When an element is considered to be "connected" to another element, it can be directly connected to the other element or an intermediate element may be present at the same time. The terms "vertical", "horizontal", "upper", "lower", "left", "right" and similar expressions used herein are for illustrative purposes only and do not mean the only implementation.

In the related art, the inside of the main body and the nozzle of the dental flusher are likely to breed bacteria because being in a humid environment all the year round, and it is easy to cause secondary pollution to the injected oral irrigating fluid, which in turn causes discomfort for the user when cleaning the dental cavity, causing poor experience of the user.

In order to solve at least one of the above technical problems, the following describes the oral irrigator provided by the embodiments of the present application with reference to the accompanying drawings.

Figure 2:
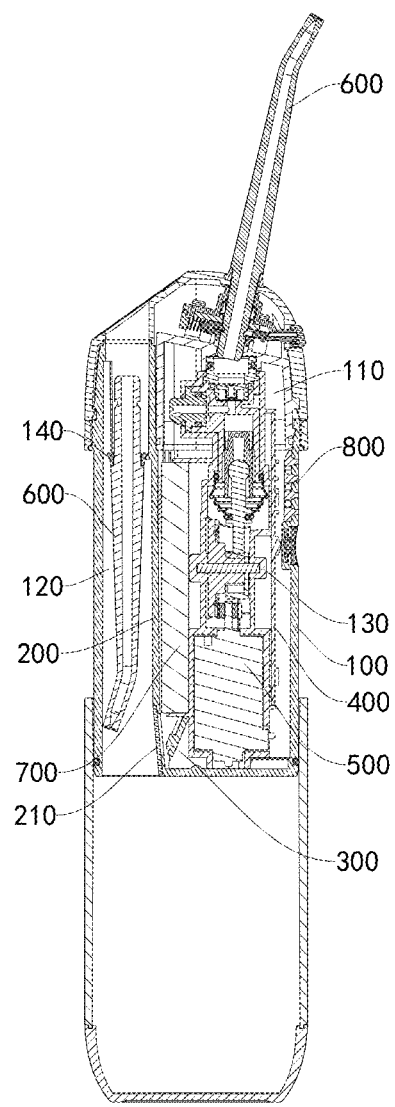
FIG. 2 is a cross sectional schematic view of the oral irrigator in FIG. 1 of the present application.

FIG. 1 shows a schematic structural view of an oral irrigator in one implementation provided by an embodiment of the present application; FIG. 2 shows a cross sectional schematic view of the oral irrigator in FIG. 1 of the present application; and FIG. 3 shows an explosion schematic view of the oral irrigator in FIG. 1 of the present application.

Figure 3:
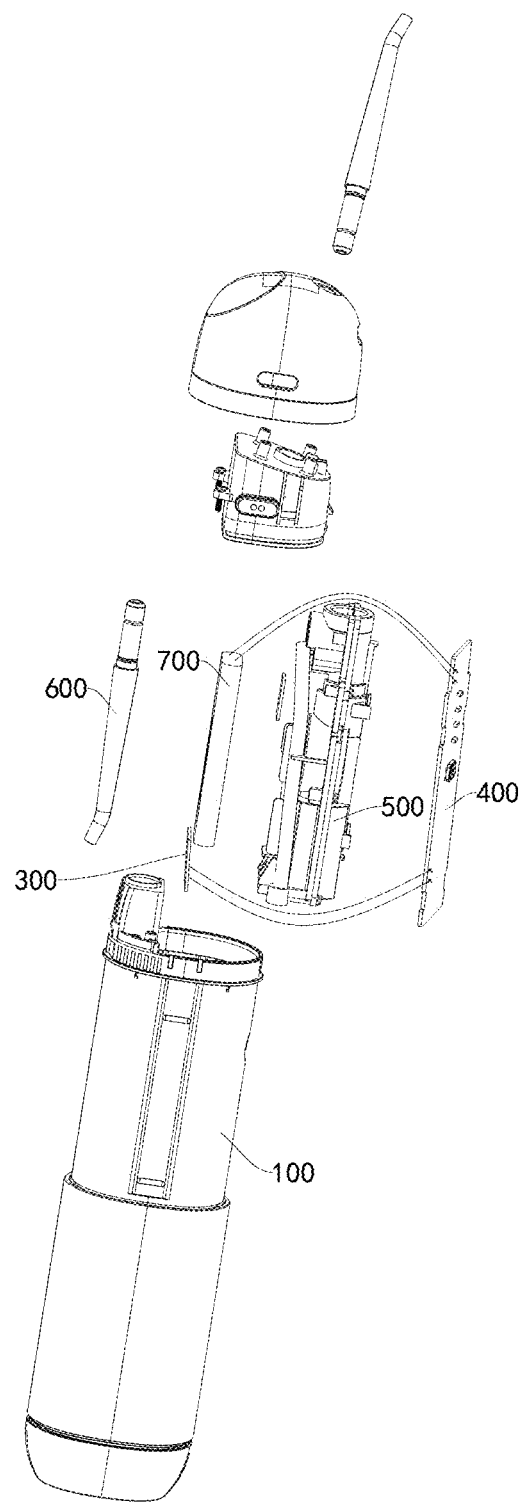
FIG. 3 is an explosion schematic view of the oral irrigator in FIG. 1 of the present application.

Referring to FIGS. 1 to 3, an embodiment of the present application provides a oral irrigator. The oral irrigator includes a main body 100, a partition wall 200, a sterilization portion, and a control main board 400. The main body 100 is provided therein with a cavity. The partition wall 200 is arranged in the cavity along the longitudinal direction of the main body 100 to divide the cavity into a first cavity 110 and a second cavity 120 spaced apart from each other. The first cavity 110 is used for accommodating the working part 500. The second cavity 120 is used for accommodating the spray head 600. It is understandable that the working part 500 herein is a mechanical part used to realize the basic oral irrigating function of the oral irrigator, because some mechanical parts that realize the oral irrigating function of the oral irrigator are in the prior art and are not described in the embodiment of the present application. The focus of the protection is not repeated here on the specific structure and working principle of the working part 500. At the same time, in FIGS. 1 to 3, the parts for holding dental fluid that is detachably connected to the main body 100 are not marked. Similarly, since these parts are prior art and not implemented in the present application The key point of the protection of the example, the specific structure and working principle of the part used to hold the dental fluid will not be repeated here.

The sterilization portion is located in the first cavity 110 and is adjacent to the partition wall 200. The sterilization portion includes an ultraviolet light UV lamp module 300. The partition wall 200 is provided with a light-transmitting area 210, such that the light emitted by the UV lamp module 300 passing through the light-transmitting area 210 to irradiate an inside of the second cavity 120 and the spray head 600.

The control main board 400 is electrically connected to the UV lamp module 300. The control main board 400 is provided with a control switch group which is electrically connected to the control main board 400. The control switch group includes a UV control switch. The UV control switch is used to control the UV lamp module 300 to turn on and off.

In order to prevent the UV lamp module 300 that is still in the on state from radiating the human body when the product is turned upside down, in some embodiments, the control switch group further includes an anti-inversion switch electrically connected to the control main board 400, and the anti-inversion switch is configured to response to turning off the UV lamp module 300 when the oral irrigator is in an tilted or inverted posture, the safety is improved.

In order to facilitate the use of user and save the cumbersome actions of turning on and off the UV lamp module 300, in some embodiments, the control switch group further includes a timing switch electrically connected to the control main board 400, and the timing switch is configured to turn off the UV lamp module 300 after the preset time period.

In some embodiments, for ease of use, the main body 100 is provided with a switch button 800 electrically connected to the control switch group.

It is understandable that the anti-inversion function, control switch function, and timing switch function implemented in the control main board 400 and the control switch group herein are the prior art and are not the focus of protection required by the embodiments of the present application. The specific structure and working principle of the control main board 400 and the control switch group will no longer be described in detail herein.

In some embodiments, in order to divide the working area of the first cavity 110 to facilitate the layout of various components, the first cavity 110 is provided with a support member 130, and the sterilization portion and the control main board 400 are fixed in the first cavity 110 by the support member 130 to realize the fixation of the sterilization portion and the control main board 400. It is understandable that the fixation here can be detachable connection or non-detachable connection, as long as it can be fixed. It can be fixed. As an embodiment, in order to facilitate installation and fixation and separate a clear working area, the support member 130 is arranged outside the working part 500 to separate the working part 500 from the sterilization portion and the control main board 400 for convenience wiring and the like are performed between the sterilization portion and the control main board 400.

In some embodiments, in order to better realize the compatibility of sterilization and disinfection, and realize the separation of the spray head 600 from the second cavity 120 for placing the spray head 600, reduce the contact area, and prevent the bacteria that may be generated from cross-contamination. The second cavity 120 is provided with an engagement portion 140, and the spray head 600 is suspended in the second cavity 120 by means of the engagement portion 140. As an embodiment, as shown in FIG. 2, the engagement portion 140 is disposed near the opening of the second cavity 120, the input end of the spray head 600 is engaged to the engagement portion 140, and the output end of the spray head 600 passes through the engagement portion 140 and is suspended in an area close to the bottom of the second cavity 120. It is understandable that, as another embodiment, the engagement portion 140 may be disposed near the bottom of the second cavity 120 and the input end of the spray head 600 passes through the engagement portion 140 and is suspended in an area close to the bottom of the second cavity 120. As long as the spray head 600 can be suspended in the second cavity 120, any arrangement that can realize this installation method is acceptable, which is not limited herein.

In some embodiments, in order to achieve a more precise disinfection effect, the position of the light-transmitting area 210 corresponds to the output end of the spray head 600, so that the ultraviolet light emitted by the UV lamp module 300 penetrates the light-transmitting area 210 to reach the output of the spray head 600, so as to disinfect the output end of the spray head 600, which is most likely to breed bacteria, to achieve a better disinfection effect. As an embodiment, when the engagement portion 140 is disposed near the opening of the second cavity 120, the input end of the spray head 600 is engaged to the engagement portion 140, and the output end of the spray head 600 passes through the engagement portion 140 and is suspended in an area close to the bottom of the second cavity 120, the light-transmitting area 210 is provided at the bottom of the partition wall 200 to correspond to the output end of the spray head 600 close to the bottom of the second cavity 120. As long as the position of the light-transmitting area 210 corresponds to the output end of the spray head 600, which is not limited herein.

In order to achieve a better light transmission effect in the light-transmitting area 210, in some embodiments, the light-transmitting area 210 is provided with an opening, and a light-transmitting plate is provided in the opening. The light-transmitting plate is a quartz glass plate. As an embodiment, the transparent quartz glass plate can achieve better light transmission effect. Because quartz glass is a special industrial technical glass with a single component of silicon dioxide, this glass has a hardness of up to 7 on the Mohs scale, and has high temperature resistance, low expansion coefficient, thermal shock resistance, chemical stability and good electrical insulation property, and can transmit ultraviolet and infrared rays. In addition, the quartz glass plate has high spectral transmission and will not be damaged by radiation (other glass will become dark after being irradiated by radiation), so the quartz glass plate can be used as the light-transmitting plate. At the same time, the quartz glass plate has an IPX7 waterproof rating, IPX7 waterproof refers to the anti-immersion type, under the specified conditions, even if it is immersed in water, it will not enter the interior. The IPX7 waterproof rating means that the product has a waterproof rating of 7, which means that the product is placed in a water depth of 1 meter. After soaking for 30 minutes, the product can be used normally without being affected. It has good moisture and dust resistance and prevents the liquid brought in by the spray head 600 placed in the second cavity 120 from entering the first cavity 110.

In some embodiments, the UV lamp module 300 includes a substrate and UV lamp beads, and UV lamp beads are provided on the side of the substrate facing the light-transmitting area 210, so that the ultraviolet light emitted by the UV lamp beads is directly emitted toward the light-transmitting area 210, thereby the disinfection efficiency of the UV lamp module 300 is improved.

In some embodiments, the device further includes a battery 700 arranged in the first cavity 110, and the battery 700 is electrically connected to the control main board 400. In other embodiments, a USB interface charging can also be used to provide power. As long as some setting methods for supplying power can be realized, which is not limited here.

On the basis of the foregoing embodiments, the working principle of the oral irrigator provided in the embodiments of the present application is as follows:

The battery 700 supplies power to the control main board 400, and the control main board 400 controls the turning on of the UV lamp module 300, and the UV lamp module 300 emits ultraviolet light, which disinfects the spray head 600 and the second cavity 120 through the light-transmitting area 210. Since the control main board 400 is provided with the anti-inversion switch, when the product is tilted more than 90 degrees or upside down, the anti-inversion switch on the control main board 400 will be triggered and the UV lamp module 300 will be automatically turned off. The control main board 400 is equipped with a timing function, when the UV lamp module 300 works for the set specified time, the UV lamp module 300 will automatically shut down. A UV control switch is disposed on the control main board 400, and during the working period of the UV lamp module 300, the UV lamp module 300 can be stopped by manually touching the UV control switch.

In summary, by arranging the partition wall 200 to separate the first cavity 110 and the second cavity 120 spaced apart from each other, the spray head 600 is separated and housed in the second cavity 120 and the first cavity 110 is provided with the sterilization portion corresponding to the second cavity 120. The sterilization portion includes a UV lamp module 300. The second cavity 120 and the spray head 600 are disinfected and sterilized by the UV lamp module 300, which effectively reduces the secondary pollution of the flushing fluid. Since the sterilization portion is built into the main body 100, and while it can be disinfected and sterilized, the ultraviolet light emitted by the UV lamp module will not directly hit the eyes and human skin, and it is not easy to be touched by people, which has a certain degree of safety. At the same time, there is an anti-inversion function, which can avoid the radiation to the human body when the UV lamp module 300 is turned on when being tilted, improving safety, and the device is further equipped with a timing shutdown function, which automatically turns off within a specified time, saving tedious operations.

The technical features of the above-mentioned embodiments can be combined arbitrarily. In order to make the description concise, all possible combinations of the various technical features in the above-mentioned embodiments are not described. However, as long as there is no contradiction in the combination of these technical features, all should be considered as the scope of the specification.

The above-mentioned embodiments only express a few implementation modes of the present application, and the description is relatively specific and detailed, but it should not be understood as a limitation to the scope of the present application. It should be pointed out that for those skilled in the art, without departing from the concept of the present application, several modifications and improvements can be made, and these all fall within the protection scope of the present application. Therefore, the protection scope of the present application should be subject to the appended claims

What is claimed is:

1. An oral irrigator, comprising:
a main body, provided therein with a cavity;
a partition wall, arranged in the cavity along a longitudinal direction of the main body to divide the cavity into a first cavity and a second cavity spaced apart from each other, wherein the first cavity is configured for accommodating a working part, and the second cavity is configured for accommodating a spray head, when the spray head is accommodated in the second cavity, an output end of the spray head is arranged adjacent to a bottom of the second cavity;
a sterilization portion, located in the first cavity and arranged adjacent to the partition wall, wherein the sterilization portion comprises an ultraviolet light UV lamp module, the partition wall is provided with a light-transmitting area, such that light emitted by the UV lamp module passing through the light-transmitting area to irradiate an inside of the second cavity and the spray head, wherein the light-transmitting area is arranged at a lower portion of the partition wall, and the UV lamp module is arranged facing the light-transmitting area, such that the light emitted by the UV lamp module only passes through the light-transmitting area and directly reach the output end of the spray head; and
a control main board, electrically connected to the UV lamp module, wherein the control main board is provided with a control switch group electrically connected to the control main board, and the control switch group comprises a UV control switch configured for controlling on and off of the UV lamp module.

2. The oral irrigator according to claim 1, wherein the control switch group further comprises an anti-inversion switch electrically connected to the control main board, and the anti-inversion switch is configured to respond to turn off the UV lamp module when the oral irrigator is in a tilted or inverted posture.

3. The oral irrigator according to claim 1, wherein the control switch group further comprises a timing switch electrically connected to the control main board, and the timing switch is configured to turn off the UV lamp module when a preset time period is reached.

4. The oral irrigator according to claim 1, wherein a support member is provided in the first cavity; and the sterilization portion and the control main board are fixed in the first cavity through the support member.

5. The oral irrigator according to claim 4, wherein the support member is arranged outside the working part to space the working part with the sterilization portion and the control main board.

6. The oral irrigator according to claim 1, wherein an engagement portion is provided in the second cavity, the spray head is suspended in the second cavity by means of the engagement portion.

7. The oral irrigator according to claim 1, wherein a position of the light-transmitting area corresponds to an output end of the spray head.

8. The oral irrigator according to claim 1, wherein the UV lamp module comprises a substrate and UV lamp beads adhered to the substrate, and the UV lamp beads are provided on a side of the substrate facing the light-transmitting area.

9. The oral irrigator according to claim 1, wherein the light-transmitting area is provided with an opening, a light-transmitting plate is provided in the opening; and light-transmitting plate is a quartz glass plate.

10. The oral irrigator according to claim 1, further comprising a battery arranged in the first cavity, and the battery is electrically connected to the control main board.

* * * * *